United States Patent [19]

Kovacs

[11] Patent Number: 5,068,240

[45] Date of Patent: Nov. 26, 1991

[54] ANTITUMOR PHARMACEUTICAL COMPOSITIONS AND PROCESS FOR PREPARING THE SAME

[76] Inventor: Ádám Kovacs, Buza u 2, H-2097 Pilisborosjenö, Hungary

[21] Appl. No.: 533,943

[22] PCT Filed: Dec. 18, 1984

[86] PCT No.: PCT/HU84/00062

§ 371 Date: Aug. 20, 1985

§ 102(e) Date: Aug. 20, 1985

[87] PCT Pub. No.: WO85/02769

PCT Pub. Date: Jul. 4, 1985

Related U.S. Application Data

[63] Continuation-in-part of Ser. No. 346,369, Apr. 28, 1989, abandoned, which is a continuation of Ser. No. 770,349, Aug. 20, 1985, abandoned.

[30] Foreign Application Priority Data

Dec. 20, 1983 [HU] Hungary .............................. 4348/83

[51] Int. Cl.$^5$ ..................... A61K 31/21; A61K 31/26; A61K 31/415
[52] U.S. Cl. ...................................... 514/401; 514/516
[58] Field of Search ............................... 514/401, 516

[56] References Cited

U.S. PATENT DOCUMENTS 3,085,940 4/1963 Cufcik et al. ...................... 514/616

FOREIGN PATENT DOCUMENTS 905186 9/1962 United Kingdom ............... 514/616

Primary Examiner—Stanley J. Friedman
Attorney, Agent, or Firm—Fitch, Even, Tabin & Flannery

[57] ABSTRACT

A pharmaceutical composition and process for preparing the same is provided, wherein the active ingredient of the said composition is one or more compounds of the general formula /I/

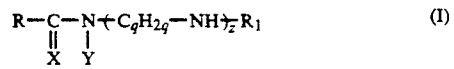

(I)

In the formula
R is longer aliphatic hydrocarbon radical which may contain one or more unsaturation,
$R_1$ is hydrogen or longer aliphatic acyl radical which may contain one or more unsaturation,
X is oxygen and Y is hydrogen, or
X and Y, when taken together, form a radical of the formula $=N-CH_2-CH_2-$,
z is 1 to 5, and
q is 1 to 4.

The use of the above compounds in the therapy of tumorous diseases and for regenerating tumorous cells and tissues is also claimed.

13 Claims, No Drawings

ANTITUMOR PHARMACEUTICAL COMPOSITIONS AND PROCESS FOR PREPARING THE SAME

This application is a continuation-in-part of U.S. Ser. No. 07/346,369, filed Apr. 28, 1989, which is a continuation of U.S. Ser. No. 06/770,349, filed Aug. 20, 1985, both are now abandoned.

TECHNICAL FIELD

The present invention relates to antitumour pharmaceutical compositions and process for preparing the same. Another object of the present invention is the use of certain polyamine derivatives having a molecular weight of not higher than 800 in the therapy of diseases connected with cellular proliferation.

BACKGROUND ART

Compounds of the general formula

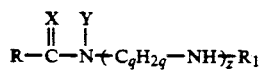

are known in the literature and used in many different industrial fields. Thus, e.g. N-[2-[2-(heptadecenyl)-2-imidazolin-1-yl]-ethyl]-oleamide is known from GB Pat. No. 929,397 as additive for polyepoxydbitumens. J. Chem. Res. Synop. 1981/3/84-5 and DE-OS No. 2,546,180 disclose the reactions of different steric isomers of N-[2-[2-(8-heptadecenyl)-4,5-dihydro-1H-imidazol-1-yl]-ethyl]-9-octadecenamide and the use thereof in the floatation of Nb/Ta minerals. The article of Przem. Chem. 46/8/, 479-81 describes the (1:1) mixture of N,N'-[ethylenebis(iminoethylene)]bis(9,11-octadecadienamide) and -(9,11-octadecadienoate) and the use thereof as cationic surfactant. According to U.S. Pat. No. 3,337,459 N,N'-[iminobis(ethyleneiminoethylene)]bis(10-octadecenamide) is used as lubricant. U.S. Pat. No. 3,193,454 describes 1,1'-(iminodiethylene)bis[2-(heptadecenyl)-2-imidazoline as additive for paints.

There is, however, no reference at all in the prior art to any therapeutical effect of the aforementioned compounds.

The last 100 years brought basic changes in the human environment, especially as a result of the extraordinary development of chemistry. Of course, this development started in unfavourable phenomena as well, and one of these is the rapid increase of tumorous diseases.

At present, cancer research is one of the most developing research areas and needs extraordinary financial and mental supply. Besides basic research, there are great efforts in the therapy of certain specific types of tumorous diseases. In many cases, chirurgical intervention is often accomplished by other kinds of therapy, e.g. irradiation, chemotherapy, etc. The known processes and especially chemotherapeutic methods have the common characteristics that they are limited in the field of specific types of tumour. No general method resulting in a general regeneration of tumorous cells has been found so far.

According to the present state of science, tumorous diseases can be cured when detected in the very early state. As the early phase is very hard to recognize, tumorous diseases belong to those which are the most difficult to cure. Generally, symptomatic treatment is performed but the recovery rate is very poor. Therefore, there is a strong need for therapeutic agents which prevent the occurance of tumorous diseases and provide general and appropriate therapeutic effect in case of developed disease at the same time.

DISCLOSURE OF INVENTION

The aim of the present invention is to provide pharmaceutical compositions which fulfills the above conditions. There is also provided a process for preparing the same pharmaceutical compositions.

A further object of the present invention is the use of the compounds of the general formula (I) as above in and for the therapy of tumorous diseases.

The invention is based on the recognition that the reason of starting of cancerous processes is due to failures in the correct information and/or circulation chain between cells. In healthy organ, permanent communication takes place between the cells. The occurance of malign processes in the organ is a result of lack of "communication channels" between cells, as the cells cannot recognize each other, lose their connections and start of multiply according to their own internal information. The multiplication is of malign degree and leads to proliferation.

It has been found that the proliferated cells having occured due to malign processes are not to be destroyed, but the possible contact between these and/or healthy cells should be re-established. The only way to re-establish the tissue structure of tumour cells into healthy tissue is to renew the intercellular communication.

Presumably, the protein shell occuring on the cell wall forms a shield on the membrane, thus, making the intercellular "communication channels" unable to operate. Starting from this theory, our investigations were directed to find materials which disintegrates the said protein shell so that the intercellular communication channels can recover and the tumour cell loses its isolation.

It has been found that the above effect can be achieved by administering an effective amount of at least one compound of Formula I to malignant cells sensitive to at least one compound of the general formula (I) as above, wherein R is a $C_{12}$ to $C_{20}$ saturated aliphatic hydrocarbon or acyl radical or an unsaturated aliphatic hydrocarbon which contains one or more carbon-carbon double bonds, $R_1$ is hydrogen or longer aliphatic acyl radical which may contain one or more unsaturation, X is oxygen and Y is hydrogen, or X and Y, when taken together, form a radical of the formula $=N-CH_2-CH_2-$, z is an integer of 1 to 5, q is an integer of 1 to 4.

It can be seen that the above compounds are straight chained polymer amino compounds, as well as the tautomers thereof, when X and Y together form a group $=N-CH_2-CH_2-$, i.e. an intermolecular dihydroimidazo ring is formed.

The above longer aliphatic hydrocarbon group contains preferably 12 to 20 carbon atoms and optionally at least one double bond. In the open chained compounds, i.e. wherein X is oxygen, the longer aliphatic acyl group is preferably derived from stearic acid, oleic acid and linoleic acid.

As already mentioned, the compounds of the general formula (I) are known in the art, or, if novel, they can be prepared by known methods, e.g. by the following reactions:

R—COOH +  I.
fatty acid

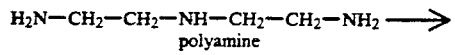

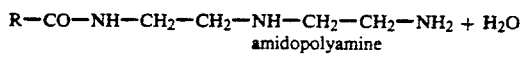

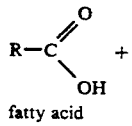  +  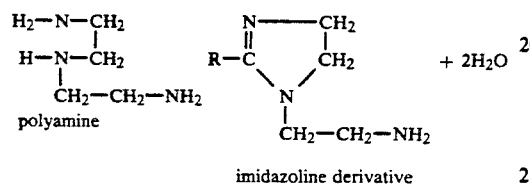  + 2H₂O  II.

fatty acid          polyamine         imidazoline derivative

Of course, the compounds of the general formula (I) having other structure than the above end products can be prepared by essentially the same routes as described hereabove.

In the pharmaceutical preparations of the present invention any of the compounds of the general formula (I), as well as the mixture of any or even all of them can be used as active ingredient. Under "active ingredient" all the possible stereoisomers of the aforesaid compounds are also to be meant.

It is to be mentioned that in aqueous medium equilibrium occurs between the open chained and tautomeric ring form.

The pharmaceutical compositions according to the present invention can be prepared by process well known for formulating compositions of this type, such as by mixing one or more compounds of the general formula (I) with a physiologically acceptable carrier suitable for oral, vapor or injection administration.

The pharmaceutical compositions according to the invention can be administered orally or preferably intravenously, another preferred administration form being the inhalation. For this purpose, the vapor of active compound according to the invention, or the mixture of more of these or that of the same formulated into inhalation composition is inhaled by the patient. In case of inhalation, the vapor phase may contain not only the vapor of the active compounds of the formula (I) but also some decomposition products. These have the general formula NRR'R" and H$_2$N-[(CRR')$_y$-NH)]$_x$-H, wherein R is hydrogen, lower alkyl or —(CH$_2$)$_n$—OH,
R' and R" are hydrogen and lower alkyl, and
n, x and y are integers.

As possible decomposition product formaldehyde should also be mentioned.

Accordingly, the pharmaceutical compositions according to the invention comprise also the formulations containing the compounds of the formula (I) and the decomposition products thereof as active ingredient.

The active compounds and the pharmaceutical compositions, resp., according to the invention induce the tumor cells and normal cells to communicate, consequently, the tumor cells again recognize their environment, further proliferation terminates and the immune system goes into action by eliminating the superfluous, but no more tumorous cells by the aid of different protective mechanisms of the organism. According to our biological tests, a mixture of the active compounds of the general formula (I) proved to be especially active in re-establishing the intercellular communication and/or circulation channels.

According to the invention, the regeneration or creation of intercellular communication and/or circulation channels may be accomplished both in vivo and in vivo. For these purposes the active compounds and compositions according to the invention, preferably the above mixture are administered via blood flow, lymphatic system orally and/or by inhalation technique.

The antitumour effect of the compounds of the general formula (I) and the mixture thereof was tested in animal and clinical experiments as well as in vitro on tissue cultures, including leukemia virus producing transformed cell lines. It has been found that transformed and malign proliferation cell lines can be brought in contact inhibition with a $10^{-5}$ to $10^{-6}$ dilution of the compounds and compositions according to the invention while the non-malignant lines are not inhibited in their multiplying. During tests carried out on mice the tumor inhibiting doses of the compounds proved to be less than 100 μg/kg body weight. At the first stage of clinical trials it was established that according to our special diagnostic method described in Hungarian Patent Application No. 78/84 considerable regeneration from the tumorous state took place.

In the aforementioned dilutions the compounds according to the invention are non-toxic, LD$_{50}$ in animal experiments is 15 mg/kg po. and 17 mg/kg when administered in the tumour, In tissue cultures the toxicity is ≦5×10⁴ dilution.

Our biological tests showed that the compositions according to the invention possess antitumor effect. Accordingly, these compositions are valuable in the therapy of tumorous diseases as well as for regenerating tumorous cells and tissues. These pharmaceutical compositions are not only useful in themselves in the therapy but can also be used to complete other techniques, like surgical operations. Moreover, they can complete or prepare the conditions of other treatments.

EXAMPLE

According to the general preparation route as described in the descriptive part, the following compounds were prepared and identified by mass spectroscopy and NMR spectroscopy methods: (In the formulae herebelow linolyl group is labelled by L and oleyl is labelled by O.)

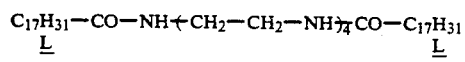

M⁺: m/z = 713

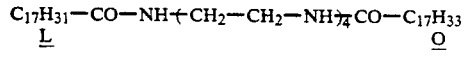

M⁺: m/z = 715

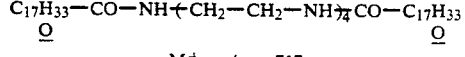

M⁺: m/z = 717

-continued $$C_{17}H_{31}\underset{\underline{L}}{-}CO-NH(CH_2-CH_2-NH)_3CO-\underset{\underline{L}}{C_{17}H_{31}}$$

$$M^+: m/z = 670$$

$$C_{17}H_{31}\underset{\underline{L}}{-}CO-NH(CH_2-CH_2-NH)_3CO-\underset{\underline{O}}{C_{17}H_{33}}$$

$$M^+: m/z = 672$$

$$C_{17}H_{33}\underset{\underline{O}}{-}CO-NH(CH_2-CH_2-NH)_3CO-\underset{\underline{O}}{C_{17}H_{33}}$$

$$M^+: m/z = 674$$

|  | M+: m/z | (W, Z) |
|---|---|---|
| H2C——N<br>\|  \|\|<br>H2C   C—W<br>  \ /<br>   N<br>   \|<br>(CH2—CH2—NH)3CO—Z | 695<br>697<br>699 | (L, L)<br>(L, O)<br>(O, O) |

|  | M+: m/z | (W, Z) |
|---|---|---|
| H2C——N<br>\|  \|\|<br>H2C   C—W<br>  \ /<br>   N<br>   \|<br>(CH2—CH2—NH)2CO—Z | 652<br>654<br>656 | (L, L)<br>(L, O)<br>(O, O) |

|  | M+: m/z | (W, Z) |
|---|---|---|
| H2C——N<br>\|  \|\|<br>H2C   C—W<br>  \ /<br>   N<br>   \|<br>CH2—CH2—NH—CO—Z | 609<br>611<br>613 | (L, L)<br>(L, O)<br>(O, O) |

$$C_{17}H_{31}\underset{\underline{L}}{-}CO-NH(CH_2-CH_2-NH)_3H \quad M^+: m/z = 408$$

$$C_{17}H_{33}\underset{\underline{O}}{-}CO-NH(CH_2-CH_2-NH)_3H \quad M^+: m/z = 410$$

|  | M+: m/z | W |
|---|---|---|
| H2C——N<br>\|  \|\|<br>H2C   C—W<br>  \ /<br>   N<br>   \|<br>(CH2—CH2—NH)2H | 390<br>392 | L<br>O |

The NMR ($^1$H, $^{13}$C and $^{15}$N) spectroscopy confirmed the above structures.

The above compounds (hereafter called CDM) as well as the mixture thereof were tested in the following biological arrangements:

In vitro tests were carried out to answer the following problems:

What is the effect of CDM on the proliferation of cells with or without malignant transformation in vitro. Investigations were first performed on cell lines in the log. phase (logarithmic growth phase; experiments type A), thereafter on cells being in the plateau phase (hardly proliferating cells, experiments type B);

Determination of the biologically effective dilution range. The applied doses were not expressed in concentrations but in dilution units;

Investigations of the in vitro cytotoxicity of CDM, and the reversibility of this effect.

The following materials and methods were applied in these experiments;

CELL LINES

Cell lines of normal tissue origin: McCoy's human monolayer cell line of synovial origin, BHK fibroblast type monolayer cell line of newborn hamster kidney origin, in BHK-B and in BHK-Tübingen varieties, HAK monolayer cell line of adult hamster kidney origin, MRC-5 monolayer cell line of human embrional lung origin.

Cell lines of tumour origin: LLC monolayer cell line of human bronchial carcinoma origin (maintainable also in vivo, in mice) containing 70–80% epitheloid type cell, HeLa-S3 a clone of a cell line of human cervical carcinoma origin, K 562 a cell line of erythroid leukemia origin, growing in suspension, SP 2 a suspension clone of mouse myeloid leukemia origin, P-388 a suspension cell line of mouse lymphoid leukemia origin, L-1210 a cell line of mouse lymphoid leukemia origin (it is maintainable in ascitic form, too).

CULTURING CONDITIONS

Cell lines were maintained in Minimum Essential Medium (MEM) containing 10% fetal calf serum (FCS, Flow Laboratories Ltd.). In order to avoid bacterial infection 50 µg/ml gentamycin (SERVA) was added. The cultures were maintained in 25 cm$^3$ Falcon plastic cell culture vessels (NUNC, Greiner or Costar) in 10 ml volumes.

Monolayer cultures were transferred with the addition of 0.05% trypsin, while suspension cultures were diluted. For tests on CDM cell culture, multiplates containing 24 wells of 2 cm$^3$ were used with the addition of 1 ml medium/well. The cultures were grown for 72 hours at 37° C. in an atmosphere containing 5% CO$_2$. Relative humidity was kept at 75–80%. Cell cultures in log. phase were achieved by tenfold dilution of cultures being in plateau phase and showing contact inhibition. In monolayer cultures, the condition of contact inhibition was considered to occur on day following the microscopic appearance of cell confluence. These cultures were used in B-type experiments.

DILUTION OF CDM

CDM was diluted in MEM (without serum), starting from thousand fold dilution of the stock solution. The proper fine dispersity of the emulsion was achieved by a lasting intense mixing using a Vortex mixer. Before the addition to the cultures the given dilutions were carefully rehomogenized.

Cell counting was performed by Bürker's hemocytometer or, if also cytofluorometric measurement was performed out the values of the Cytofluorograph were automatically accepted.

FLOW-MICROFLUOROMETRIC MEASUREMENTS

After trypsinization cells were centrifuged and stained in ice cold isotonic trisodiumcitrate containing 50 µg propyl iodide for 30 minutes. Measurements were performed using a Cytofluorograph (Bio/Physics Inc.) with the aid of an Ar ion gas laser at 488 nm. The fluorescence of propyl iodide-DNA complex was detected above 600 nm.

By means of a built-in electronic differential discriminator, cells having less than "diploide" DNA content were discarded, because these cells very probably died long before the measurement.

DETERMINATION OF VIABILITY

After trypsinization cells were suspended in MEM medium containing 0,05% w/v trypan-blue stain. Five minutes later the number of living (excluding trypan-blue) cells and dead cells (becoming blue) was determined by light microscopy.

DETERMINATION OF REVERSIBILITY

Cell cultures were treated for 24 hours with CDM. At this time half of the parallel samples were analysed, while the rest were re-incubated in a fresh medium containing no CDM. After 24 hours recultivation was stopped and the cells were removed for analysis.

RESULTS

CDM was first investigated on log. phase cell cultures. Optimal dose range for further studies was selected on SP 2 cell line, where CDM was applied at a wide concentration range.

On the basis of these experiences in further works a dilution range of $5 \times 10^4 - 10^7$-fold was used.

According to the modification of the growth curves, our test systems can be grouped as follows:

$5 \times 10^4$-fold dilution of CDM killed the cells of the culture by the 24th hour (K-562, MRC-5, BHK-B, McCoy, HAK, SP 2);

$5 \times 10^4$-fold dilution of CDM killed the cells of the culture by the 48th hour of experiment (P-388, L-1210, BHK-Tüb.);

no detactable toxic effect at the investigated dilution range (HeLa, LLC). Certain concentrations of CDM even stimulated the growth of cells of the two later lines being in the log. phase.

The effect of CDM on cultures being at the contact inhibition phase was investigated in two series. It was found that the effects of CDM were reversible in dilutions over $10^5$-fold, while in dilutions under $10^4$-fold it seemed to be irreversible. One part of the growth-response curves, registered after a 72 hour culture period showed a continuous charge (BHK-B, BHK-Tüb., HAK, L-1210), while others had a local minimum point (SP 2, McCoy, LLC, HeLa, MRC-5, P-388). Most of the local minimum points were within the $10^5$-$10^6$-fold dilution range.

Viability studies were performed on four cell lines (LLC, McCoy, HeLa, BHK-Tüb.) at a dilution range of $5 \times 10^3$-$10^6$. In $10^4$-fold or lower dilutions CDM resulted in 100% toxicity. The in vitro $LD_{50}$ values fell between $10^4$ and $5 \times 10^4$-fold dilution.

In further tests, the leukemia virus producing QL transformed cell line (Nagy, K.: Chester Beatty Seminars (London) 1983) was chosen to study the effects of CDM in vitro.

MATERIALS AND METHODS

Because of the alkaline nature of the material CDM was not applied directly, but first diluted in dimethyl-sulfoxide (DMSO, Reanal) and its further dilutions were used.

CELL CULTURE

The transformed quail fibroplast cell line (QL) continuously produce MD 29/L virus subline of increased oncogenicity.

Cells were maintained and propagated in Falcon-type plastic culture flasks. Parker 199 tissue culture medium completed with 10% tryptose-phosphate, 5% fetal calf serum and 1% chicken serum, was used. Cell cultures were incubated at 37° C. in an atmosphere containing 5% $CO_2$ in air. Cell cultures were transferred by trypsinization usually every other day.

CELL COUNTING

Cell cultures were dispersed by trypsinization and the cell counts were determined by a Laborscal (Labor MIM) electronic cell counter or in a few cases, using the conventional Buerker's method.

VIABILITY

Cell counts were corrected according to the proportion of living cells. This was determined using the trypan blue exlusion technique.

DETERMINATION OF $^3$H-THYMIDINE INCORPORATION

The rate of DNA synthesis was determined after CDM treatment by means of the addition of 50 $\mu$Ci (0,2 ml) radioactive $^3$H-thymidine nucleoside (Thymidine-6-$^3$H, Chemopol, Czecho-Slovakia) to the cultures ($10^6$ cells vessel).

At selected intervals cell suspensions were washed with culture medium and after centrifugation (2000 rpm, 5 min., $+4°$ C.) cells were precipitated with 5 ml 5% ice cold trichloroacetic acid and collected on Millipore filter. The radioactivity of the samples were determined using Packard Tricarb scintillation counter.

REVERSE TRANSCRIPTASE (RT) ASSAY

In the culture medium of QL cells the presence and titer of the MC 29/L virus was determined by the RT enzyme activity characteristic only to RNA tumour viruses. Culture medium was first cleared from cell debris by centrifugation (10,000 g, 30 min., $+4°$ C.). Virus fraction was then concentrated by ultra-centrifugation (100,000 g, 90 min., $+4°$ C.); (MSE 65 Super Speed, U.K.).

Sediment was resuspended in the following buffer solution: 0,01M Tris-HCl pH 7,5, 0,1M NaCl and 0,001M EDTA. The reaction was carried out as described earlier in Acta Microbiol. 25, 142 (1978). Briefly: reaction mixture containing TKD buffer, $McCl_2$ Triton-X 100 and thymidine-triphosphate was incubated with poly (rA) (dT)$_{12}$ template-primary in the presence of the virus. The synthesized DNA was precipitated by TCA on filter discs and their activity was determined by a scintillation counter.

IMMUNOFLUORESCENCE

The state or alterations of active filaments, which build up the skeleton of the cell—cytoskeleton—were studied by indirect immunofluorescence in normal, transformed and CDM treated cells. Cells were grown on thin round cover glasses and incubated with anti-actin rabbit serum at 37° C. for 40 minutes. After abundant washing incubations continued with second antibodies, either with fluorescein or with rhodamin conjugated anti-rabbit goat serum. After the second antibody conjugation, samples were examined by fluorescence microscopy, in ultraviolet light.

TOXICITY TEST

Two day old QL fibroblast cultures containing $10^6$ cells were treated with various concentrations of CDM diluted in DMSO. The diluted material was added to the vessels in one ml volume. 48 hours later cell count and viability were determined. Toxocity test revealed, that $10^3$, $10^4$ and $10^5$-fold dilutions of CDM were highly cytotoxic, since they decreased significantly the number and viability of living QL cells. Even the $10^6$-fold dilution resulted in cell count decrease, although it was not significant. There was practically no decrease in cell count or viability at $10^7$ or higher dilutions, so these dilutions can be considered as non-toxic for QL cells.

INHIBITION OF CELL PROLIFERATION

The effect of CDM was studied on the kinetics of rapidly proliferating transformed QL cells. Untreated cells doubled their number every second day.

Cell proliferation was highly influenced by the various concentrations of CDM.

The $10^7$-fold dilution did not alter the characteristics of the proliferation, however, longer time was needed to produce the same number of cells as compared to controls. The effect of the $10^6$-fold dilution is interesting. Cell-division started slowlier, but its intensity was constant until the 6th day. From that time the proportion of divisions increased and on day 8 it was close to the value of the former dilution. The effect of the $10^5$-fold dilution was opposite. First a slow proliferation started, but it stopped on day 4 and from this day on the cell count gradually decreased. The $10^4$ dilution resulted in this effect already on the second day of treatment.

INTENSITY OF DNA SYNTHESIS

The intensity of DNA synthesis was measured by the incorporation of a radioactive nucleoside-thymidine into proliferating treated and untreated cells. Day by day increasing incorporation was found in untreated cells. The rate of increase was diminished on the days 5, 6. At $10^7$-fold dilution a variable degree of increase and decrease of thymidine incorporation was observed, nevertheless it showed still an overall slow increase. $10^6$ dilution moderately decreased the intensity of DNA synthesis of QL cells while $10^5$-fold dilution caused a very considerable decrease.

REVERSE TRANSCRIPTASE ASSAY

Besides studying the effect of CDM on the intensity of DNA synthesis and cell proliferation we wanted to study the influence of the compound on the propagation of tumour viruses produced by QL cells. On the indicated days samples were taken from the culture media and reverse transcriptase enzyme activity, characteristic to tumour viruses, were determined. $10^7$-fold dilution of CDM decreased the enzyme activity which is proportional to virus concentration, as compared to untreated cells, but the values showed an increasing tendency in the function of time.

At $10^6$-fold dilution, there was a certain initial increase but it declined on day 6 (3rd measurement) and measurements revealed a strongly decreased virus concentration. $10^5$ dilution completely inhibited virus propagation, on the sixth, and eighth days there were no enzyme activity detectable.

ALTERATION OF CYTOSKELETON ACTIN FILAMENTS

The skeleton of superior cells is the cytoskeleton. This is a complex network of protein filaments in the cytoplasm. The main constituents are actin filaments. The presence and alternations of them were investigated in normal, virus transformed and CDM treated fibroblasts.

In normal fibroblasts they form strong, organized fascicles, these actin fascicles can be observed all over the cytoplasm. Cells transformed by ONCORNA viruses show a totally different morphological appearance. In these cells actin filaments become fibrillous, they may form knots, they are situated irregularly without any order, and might be present or missing in any parts of the cytoplasm.

After CDM treatment cells had again a distinct morphological appearance and had outgrowths. The formerly broken precipitated actin particles were organized into filaments, though the orientation of the filaments was not so expressed yet as found in normal cells. For the sake of more complete demonstration the actin filaments of cytoskeleton were stained with rhodamin, instead of fluorescein, and basically similar process was demonstrated.

The pharmacological effect of CDM was tested on Swiss white mice inoculated with tenfold dilution series of Németh-Kellner lymphoma (NKL). The groups of mice were inoculated with the dilutions of NKL and the CDM material at the same time, at the start of the experiment. The animals were then treated with CDM during the test for 5 additional occasions. The animals serving for control were injected with dilutions of the NKL material at the start. These animals were not treated otherwise.

The average weight of CDM treated and control animals were compared six times during the experiment. The average weight of CDM treated animals on the 16th day was by 8 to 27% less than that of the control.

On the 18th day the animals were exterminated and dissected. In case of mice inoculated with undiluted NKL (50 million cells/animal) CDM did not inhibit the tumour formation. On the groups inoculated with $5\times10^6$, $5\times10^5$ and $5\times10^4$ or less cells, resp., CDM provided a protection of 20%, 80% and 100%, resp.

I claim:

1. A method for the treatment of a patient affected by malignant cells which are sensitive to a compound of formula I, said method comprising administering to the patient a composition comprising a physiologically acceptable carrier and at least one compound of formula I in an amount which is effective for the control of said sensitive malignant cells, said at least one compound having the general formula:

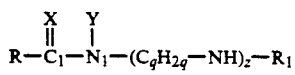

$$R-\overset{X}{\underset{\|}{C_1}}-\overset{Y}{\underset{|}{N_1}}-(C_qH_{2q}-NH)_z-R_1 \qquad I$$

wherein

R is a saturated or unsaturated aliphatic hydrocarbon group having twelve to twenty carbon atoms;

$R_1$ is hydrogen or a saturated or unsaturated acyl radical having twelve to twenty carbon atoms;

X is oxygen;

Y is hydrogen, or

X and Y, when taken together, form a bridging radical of formula $=N-CH_2-CH_2-$ wherein the nitrogen of the bridging radical is bonded to $C_1$ and the other end of the bridging radical is bonded to $N_1$;

z is 1 to 5; and q is 1 to 4.

2. A method as recited in claim 1, wherein R has 16 to 18 carbon atoms, $R_1$ is an acyl radical having 17 to 19 carbon atoms, z is 1 to 4 and q is 2.

3. A method as recited in claim 2 wherein R is an aliphatic hydrocarbon radical of an acid selected from the group consisting of stearic acid, oleic acid and linoleic acid, and $R_1$ is selected from the group consisting of hydrogen, stearyl, oleyl and linoleyl group.

4. A method as recited in claim 2 wherein $R_1$ is unsaturated.

5. A method as recited in claim 1 wherein said malignant cells are cells selected from the group consisting of leukemia cells, lymphoma cells and carcinoma cells.

6. A method as recited in claim 2 wherein said malignant cells are cells selected from the group consisting of leukemia cells, lymphoma cells and carcinoma cells.

7. A method as recited in claim 3 wherein said malignant cells are cells selected from the group consisting of leukemia cells, lymphoma cells and carcinoma cells.

8. A method as recited in claim 4 wherein said malignant cells are cells selected from the group consisting of leukemia cells, lymphoma cells and carcinoma cells.

9. A pharmaceutical composition for the treatment of malignant cells sensitive to a compound of formula I, said composition comprising a physiologically acceptable carrier and at least one compound of formula I in an amount which is effective for the control of said sensitive malignant cells, said at least one compound having the general formula:

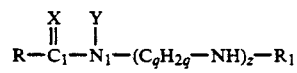

wherein

R is a saturated or unsaturated aliphatic hydrocarbon group having twelve to twenty carbon atoms;

$R_1$ is hydrogen or a saturated or unsaturated acyl radical having twelve to twenty carbon atoms;

X is oxygen;

Y is hydrogen, or

X and Y, when taken together, form a bridging radical of formula $=N-CH_2-CH_2-$ wherein the nitrogen of the bridging radical is bonded to $C_1$ and the other end of the bridging radical is bonded to $N_1$;

z is 1 to 5; and q is 1 to 4.

10. The composition of claim 9, wherein R has 16 to 18 carbon atoms, $R_1$ is an acyl radical having 17 to 19 carbon atoms, z is 1 to 4 and q is 2.

11. The composition of claim 10, wherein R is an aliphatic hydrocarbon radical of an acid selected from the group consisting of stearic acid, oleic acid and linoleic acid, and $R_1$ is selected from the group consisting of hydrogen, stearyl, oleyl and linoleyl group.

12. The pharmaceutical composition of claim 10, wherein the composition comprises a mixture of compounds of the general formula.

13. The pharmaceutical composition of claim 11 wherein the composition comprises a mixture of compounds of the general formula.

* * * * *

UNITED STATES PATENT AND TRADEMARK OFFICE
CERTIFICATE OF CORRECTION

PATENT NO. : 5,068,240            Page 1 of 2
DATED : November 26, 1991
INVENTOR(S) : Kovacs, Adam It is certified that error appears in the above-identified patent and that said Letters Patent is hereby corrected as shown below:

Column 1, line 41, change 2-(heptadecenyl)-2-imidazoline" to --2-(8-heptadecenyl)-2-imidazoline--.

Column 1, line 57, change "accomplished" to --accompanied--.

Column 2, line 22, change "of" to --to--.

Column 2, line 44, after "to" insert --the--.

Column 4, line 13, change "in vivo" (second occurrence) to --in vitro--.

Column 4, line 37, change "," (comma) to --.-- (period).

Column 5, lines 59-60, change "concentrations" to --concentration--.

Column 5, line 64, change ";" to --:--.

UNITED STATES PATENT AND TRADEMARK OFFICE
CERTIFICATE OF CORRECTION

PATENT NO. : 5,068,240
DATED : November 26, 1991
INVENTOR(S) : Kovacs, Adam

It is certified that error appears in the above-identified patent and that said Letters Patent is hereby corrected as shown below:

Column 7, line 44, change "charge" to --change--.

Signed and Sealed this

Twentieth Day of April, 1993

Attest:

MICHAEL K. KIRK

Attesting Officer     Acting Commissioner of Patents and Trademarks